United States Patent [19]

Flaningam et al.

[11] 4,411,740

[45] Oct. 25, 1983

[54] SEPARATION OF CHLOROSILANES BY EXTRACTIVE DISTILLATION

[75] Inventors: Ora L. Flaningam, Midland, Mich.; Roland L. Halm, Madison, Ind.

[73] Assignee: Dow Corning Corporation, Midland, Mich.

[21] Appl. No.: 419,854

[22] Filed: Sep. 20, 1982

[51] Int. Cl.$^3$ .............................. B01D 3/40; C07F 7/20
[52] U.S. Cl. .......................................... 203/58; 203/71; 203/88; 556/465; 556/466
[58] Field of Search ............... 203/58, 57, 84, 88, 203/71; 556/466, 472, 465

[56] References Cited

U.S. PATENT DOCUMENTS

| | | | |
|---|---|---|---|
| 2,388,575 | 11/1945 | Sauer et al. | 556/466 |
| 2,738,359 | 3/1956 | Hyde | 556/466 |
| 3,007,956 | 11/1961 | Linville et al. | 260/448.2 |
| 3,114,678 | 12/1963 | Megantz et al. | 556/466 |
| 4,012,289 | 3/1977 | Haskell | 203/58 |
| 4,024,028 | 5/1977 | Haskell | 203/58 |
| 4,162,198 | 7/1979 | Stockburger et al. | 203/58 |

FOREIGN PATENT DOCUMENTS 709630 1/1980 U.S.S.R. .................. 556/466

OTHER PUBLICATIONS

Russian Patent 165,445 appearing in *Soviets Inventions Illustrated*, Jun. 1965.
Russian Patent 275,054 appearing in *Soviets Inventions Illustrated*, Mar. 1971.
Sivtsova et al., J. Appl. Chem USSR, 38, 2549 (1966).
Sivtsova et al., J. Appl. Chem USSR, 39, 1908 (1967).
Sivtsova et al., J. Appl. Chem USSR, 41, 447 (1969).

*Primary Examiner*—Wilbur L. Bascomb, Jr.
*Attorney, Agent, or Firm*—Richard A. Kaba

[57] ABSTRACT

A method for separating close-boiling chlorosilanes by the procedures of extractive distillation using sulfolane as the extractive solvent is described. An example of close-boiling chlorosilanes which can be separated by this method include dimethyldichlorosilane and methyltrichlorosilane containing mixtures. The invention comprises heating a mixture of the close-boiling chlorosilanes with sulfolane to distill the lower-boiling chlorosilane from the mixture and thereafter separating the sulfolane and the high-boiling chlorosilane.

6 Claims, No Drawings

SEPARATION OF CHLOROSILANES BY EXTRACTIVE DISTILLATION

BACKGROUND OF THE INVENTION

During the reaction of methyl chloride with silicon a mixture of chlorosilanes is produced. These are normally separated by distillation. Two of the largest volume chlorosilanes are dimethyldichlorosilane and methyltrichlorosilane. In order to prepare satisfactory siloxane polymers from dimethyldichlorosilane it is sometimes necessary that the methyltrichlorosilane content of the dimethyldichlorosilane be less than about 500 parts per million. The boiling points of these materials are sufficiently close that distillation columns of 200 stages or more are required to satisfactorily separate these materials in commercial operation. Consequently at the present time a large capital investment is required in order to install these columns and it would be highly desirable to reduce this capital investment. Also, a large column generally requires more energy to operate than a smaller column. Careful fractional distillation is also employed by the organosilicone industry to separate other close-boiling chlorosilanes.

Thus one object of this invention is to provide a method of separating dimethyldichlorosilane and methyltrichlorosilane which uses smaller distillation columns and requires less energy thereby reducing the capital investment necessary in basic chlorosilane plants. Another object of this invention is to provide a method of separating close-boiling chlorosilances which uses smaller columns and requires less energy. Still another object of this invention is to provide a method of separating chlorosilanes which will increase the capacity of existing distillation columns of basic chlorosilane plants. Other objects of the instant invention will be apparent from this specification to those skilled in the art.

U.S. Pat. No. 3,007,956 (issued Nov. 7, 1961) predicts that one might carry out an extractive distillation of mixtures of chlorosilanes in the presence of certain dinitriles such as adiponitrile or glutaronitrile. Specifically, the patent teaches in Example 4, that, based upon beta/beta' values obtained from mixtures of dimethyldichlorosilane and methyltrichlorosilane in adiponitrile as compared to the vapor pressure of each alone, "those skilled in the art would know . . . that adiponitrile would be a suitable solvent . . . in accordance with the procedures of extractive distillation".

Sivtsova et al., *J. Appl. Chem. USSR*, 38, 2549 (1966), hereafter referred to a Sivtsova I, also discusses the problem of separating certain chlorosilanes by distillation. They measured the relative retention times of various chlorosilane mixtures with some 31 solvents on a gas chromatograph and predicted, based on relative retention times, that the materials would function as separating agents. They repeated the experiments with certain of the materials at different temperatures as shown in Table 2, p. 2551 of Sivtsova I. Among the solvents employed in Tables 1 and 2 is sulfolane (tetrahydrothiophene-1,1-dioxide). In no case did Sivtsova I carry out an actual distillation with any of the solvents nor did they obtain liquid-vapor equilibrium data.

Liquid-vapor equilibrium data at least are essential to determine whether a particular solvent, which gives promising relative retention times by gas chromatography, will actually enhance separation of the materials in question. For example, relative retention time studies alone do not predict the formation of azeotropes during actual distillation nor do they preclude the formation of a "pinch". A "pinch" is where the relative volatility approaches but is not exactly equal to 1.00 as opposed to an azeotrope where the relative volatility is exactly equal to 1.00. The formation of either an azeotrope or a "pinch" will make separation by distillation impossible from a commercial standpoint.

The inadequacy of the data in Sivtsova I is acknowledged in Sivtsova et al., *J. Appl. Chem USSR*, 39, 1908 (1967), hereafter referred to as Sivtsova II, (a subsequent publication) which admits that the investigations described in the earlier publication(Sivtsova I) "cannot give a full quanitative assessment" of the extractive distillation process. Sivtsova II further states that "liquid-vapor equilibrium data . . . are necessary for extractive distillation process calculations". In another subsequent publication, Sivtsova et al., *J. Appl. Chem USSR*, 41, 447 (1969), labeled Sivtsova III, the authors state that liquid-vapor equilibrium studies "are necessary for calculations relating to extractive distillation of these materials." Sivtsova II uses beta-beta' dichloroethylether and Sivtsova III employs ethylmonochloroacetate as the extractive solvent. Thus, in all their publications subsequent to Sivtsova I, no mention is made of sulfolane. It also does not appear in their Russian Pat. Nos. 165,445 and 275,054 appearing in *Soviets Inventions Illustrated*, June 1965, and March, 1971, respectively.

The reason for the omission of sulfolane in spite of the relative retention times shown in Table 2 of Sivtsova I, may be found on page 2549 of that publication. There the authors state, in referring to the extractive distillation use of the dinitriles of U.S. Pat. No. 3,007,956, that "these substances are extremely difficult to use because of their excessively high boiling points. For example, adiponitrile boils at 295° C. and malonic dinitrile boils at 220° C." Sulfolane boils at about 285° C. at atmospheric pressure.

There are other reasons why solvents showing high relative volatility coefficients may not be suitable for commercial separation. First, the solvent may decompose under prolonged use or it may react with chlorosilanes or both. Second, the toxicity of the proposed solvent may be too high for use in commercial operation especially in the present age of environmental concern.

SUMMARY OF INVENTION

This invention relates to a method of separating close-boiling chlorosilanes which comprises heating a mixture of the close-boiling chlorosilanes with sulfolane to distill the lower-boiling chlorosilane from the mixture and thereafter separating the sulfolane and the higher-boiling chlorosilane.

One embodiment of this invention relates to a process of separating methyltrichlorosilane and dimethyldichlorosilane which comprises mixing a mixture of the two with sulfolane and heating to remove the methyltrichlorosilane from the mixture and thereafter separating the dimethyldichlorosilane and the sulfolane.

Naturally the sulfolane employed in the present invention should be as dry as possible to minimize hydrolysis of the chlorosilanes. One method of removing residual water from the sulfolane is to dry the sulfolane over molecular sieves. To prevent the reintroduction of water, the dried sulfolane should not be exposed to water vapor.

The process of this invention is an example of extractive distillation in which sulfolane is used as the extractive solvent. It has been found that any concentration of sulfolane enhances the separation of close-boiling chlorosilane by promoting, in the case of mixtures of dimethyldichlorosilane and methyltrichlorosilane, the removal of methyltrichlorosilane from the mixture. In large scale operations it is preferred that the sulfolane be employed in amounts of 15 weight percent or higher based on the total weight of the chlorosilanes. The preferred range is from 50 to 90 weight percent sulfolane. Other examples of mixtures of close-boiling chlorosilanes which can be separated by the procedures of this invention include: dimethyldichlorosilane and ethyldichlorosilane; phenyltrichlorosilane and methylphenyldichlorosilane. By "close-boiling chlorosilanes" we mean those chlorosilanes which have boiling points within about 10° C. of each other at atmospheric pressure.

The separation can be carried out in any suitable manner such as by mixing the chlorosilanes and sulfolane in a retort and then heating to remove the lower-boiling chlorosilane. Alternatively, the vapors of the mixed chlorosilanes can be passed into the sulfolane which is maintained at a temperature above the boiling point of the lower-boiling chlorosilane. The preferred method is to pass the sulfolane countercurrently to the vapors of the mixed silanes in a distillation column or tower. The temperature of the column or tower should be regulated so that liquid sulfolane flowing to the column or tower comes into contact with the vapors of the mixed chlorosilanes rising in the column or tower and with the condensed vapors on each tray in the column or tower below the sulfolane feed point.

The method of the instant invention can be carried out at above atmospheric pressure, at atmospheric pressure, or at reduced pressures. It is preferred in the extractive distillation of mixtures of chlorosilanes possessing relatively high boiling points (at 760 mm Hg) that the distillation be carried out under reduced pressure to prevent or minimize the thermal decomposition of sulfolane. Sulfolane is reported to thermally decompose at a low rate at temperatures of 180°–220° C. Above 220° C. decomposition becomes rapid with such excessive temperatures reportly causing the sulfolane 'to crack' to a dark polymer and $SO_2$. Therefore it is preferred that the extractived distillation of phenyltrichlorosilane and methylphenyldichlorosilane using sulfolane be carried out at reduced pressures. In any event the pressure should be sufficiently low so that the reboiler temperature is not high enough to thermally decompose the sulfolane to a significant extent. The instant invention can be carried out in the presence of other silanes which may be present in the crude close-boiling chlorosilane mixture. For example, the presence of silicon tetrachloride, trimethylchlorosilane, methyldichlorosilane, and dimethylchlorosilane do not inhibit the removal of the methyltrichlorosilane from a crude mixture containing dimethyldichlorosilane and methyltrichlorosilane produced by the direct reaction of silicon metal and methyl chloride. These other silanes will distill before or along with the methyltrichlorosilane.

After removal of the lower-boiling chlorosilane, the sulfolane and higher-boiling chlorosilane mixture can be separated in any suitable manner such as by gas-liquid chromatography, distillation, or flash distillation.

The following examples are illustrative only and shall not be construed as limiting the invention.

EXAMPLE

This example shows the actual distillation of methyltrichlorosilane and dimethyldichlorosilane with and without sulfolane. The sulfolane used was dried over molecular sieves (Linde type 4A from Union Carbide). The column used was a 100 stage bubble cap column 1 inch (2.54 cm) in diameter having a water cooled condensor. The distillations were carried out in a continuous mode at a condensor pressure of one atmosphere and a reflux ratio of 80:1. The distillate was taken off the top of the column at a temperature of 67.8°±0.1° C. In each run, the chlorosilane feed was composed of 7.23% by weight methyltrichlorosilane and 92.77% by weight dimethyldichlorosilane with trace amounts of other silanes such as trimethylchlorosilane, methyldichlorosilane, and other low boiling silanes produced in the direct process. The chlorosilane feed was added to the column midway up the height of the column (stage 50) and at a temperature of 27° C. The sulfolane, when employed, was added at the top of the column (stage 100). The results are shown in the table below. Run No. 1 is a distillation without sulfolane and is included for comparative purposes only.

| Run No. | Chlorosilane Feed Rate (cc/hr) | Sulfolane Feed Rate (cc/hr) | Sulfolane Feed Temp. (°C.) | Reboiler Temp (°C.) | MeSiCl$_3$ (ppm) in Bottoms | Me$_2$SiCl$_2$ (%) in Bottoms | MeSiCl$_3$ (ppm) in Me$_2$SiCl$_2$ (Sulfolane free basis) |
|---|---|---|---|---|---|---|---|
| 1 | 53 | 0 | — | 73.8 | 9500 | 97.38 | 9756 |
| 2 | 34 | 156 | 94 | 109.7 | 320 | 10.93 | 2928 |
| 3 | 33 | 212 | 90 | 116.2 | 80 | 8.025 | 997 |

The bottoms from the 100 stage column consisted essentially of dimethyldichlorosilane and sulfolane for runs 2 and 3. The dimethyldichlorosilane was recovered from the sulfolane by distillation in a 25 stage bubble cap column at a condenser pressure of one atmosphere and a temperature of 69.3° C. There was no detectable sulfolane in the distillate.

That which is claimed is:

1. A method of separating close-boiling chlorosilanes which comprises removal, by extractive distillation, of the lower-boiling chlorosilane from the close-boiling chlorosilanes by heating a mixture of the close-boiling chlorosilanes with sulfolane to extractively distill the lower-boiling chlorosilane from the mixture and thereafter separating the sulfolane and the higher-boiling chlorosilane.

2. A method of separating close-boiling chlorosilanes which comprises removal, by extractive distillation, of the lower-boiling chlorosilane from the close-boiling chlorosilane by contacting the mixed vapors of the close-boiling chlorosilanes with sulfolane at a temperature above the boiling point of the lower-boiling chlorosilane whereby the lower-boiling chlorosilane is extractively distilled and removed preferentially from the contact zone and thereafter separating the sulfolane and the higher-boiling chlorosilane.

3. A method of separating close-boiling chlorosilanes which comprises removal, by extractive distillation, of the lower-boiling chlorosilane from the close-boiling chlorosilane by passing the mixed vapors of the close-boiling chlorosilanes through a vessel and countercurrently passing liquid sulfolane, at a temperature greater than the boiling point of the lower-boiling chlorosilane, through the vessel in intimate contact with the mixed vapors of the close-boiling chlorosilane whereby the low-boiling chlorosilane is extractively distilled and substantially removed from the vessel in vapor form and thereafter separating the sulfolane and the higher-boiling chlorosilane.

4. A method as described in claim 3 wherein the vessel is a distillation column.

5. A method as described in claim 1, 2, 3, or 4 wherein the lower-boiling chlorosilane is methyltrichlorosilane and the higher-boiling chlorosilane is dimethyldichlorosilane.

6. A method as described in claim 5 wherein the sulfolane and the higher-boiling chlorosilane are separated by flash distillation.

* * * * *